United States Patent

Liu

[11] Patent Number: 6,102,852
[45] Date of Patent: Aug. 15, 2000

[54] DISPOSABLE NASAL SPECULUM

[76] Inventor: Yen-Huang Liu, 4F, No. 18, Sec. 4, Jen-Ai Road, Taipei, Taiwan

[21] Appl. No.: 09/335,920

[22] Filed: Jun. 18, 1999

[51] Int. Cl.⁷ .................................................. A61B 17/00
[52] U.S. Cl. ........................................... 600/219; 600/235
[58] Field of Search ..................... 600/184, 201, 600/219, 220, 225, 235

[56] References Cited

U.S. PATENT DOCUMENTS

| | | | |
|---|---|---|---|
| 730,284 | 6/1903 | Monosmith | 600/235 X |
| 3,528,409 | 9/1970 | Bruder | 600/220 |
| 3,664,330 | 5/1972 | Deutsch | 600/235 X |
| 4,263,898 | 4/1981 | Wannag | 600/220 |
| 4,576,168 | 3/1986 | Jalowayski | 600/220 X |
| 5,772,582 | 6/1998 | Huttner et al. | 600/235 X |

Primary Examiner—Jeffrey A. Smith
Attorney, Agent, or Firm—Dougherty & Troxell

[57] ABSTRACT

A disposable nasal speculum, which includes a first rod member having an arched tongue at one end and a hand grip at an opposite end, a second rod member having an arched tongue at one end and a hand grip at an opposite end and a 90° bend on the middle, a flexible short rod connected between the bend of the second rod member and a middle part of the first rod member, wherein the second rod member having a projecting strip extended from its inner side and stopped at an inner side of the first rod member to support the rod members in a closed position.

4 Claims, 2 Drawing Sheets

DISPOSABLE NASAL SPECULUM

BACKGROUND OF THE INVENTION

The present invention relates to a nasal speculum for stretching open the nasal passage for examination/treatment, and more particularly to such a nasal speculum which is disposable.

FIG. 1 shows a nasal speculum according to the prior art. This structure of nasal speculum is comprised of two blades A and B pivoted together by a pivot C, and a spring member E connected between the blades A and B. The blades A and B each have a front end terminating in a respective tongue D. When the user squeezes the blades A and B with the hand against the spring member E, the tongues D of the blades A and B are forced away from each other to stretch open the nasal passage. When the pressure is released from the blades A and B, the spring power of the spring member E automatically pushes the blades A and B back to their former position. This structure of nasal speculum is function. The physician can operate the nasal speculum with one hand, and examining or treating the nasal passage with the other hand. However, before or after each use, the nasal speculum must be well sterilized to prevent contamination. It is complicated to sterilize the nasal speculum before each use. Further, sterilizing the nasal speculum before each use cannot absolutely prevent contamination. In order to prevent contamination, it is suggested to use a disposable nasal speculum.

SUMMARY OF THE INVENTION

The present invention has been designed under the circumstances in view. It is therefore the main objective of the present invention to provide an inexpensive nasal speculum, that is disposable. According to one aspect of the present invention, the nasal speculum is comprised of first and second rod members, each rod member having a front end terminating in a tongue and a rear end terminating in a hand grip, a flexible connecting rod connected joining the rod members, and a projecting strip having a fixed end formed integral with the second rod member and a free end supported on the first rod member. According to another aspect of the present invention, the rod members, the connecting rod, and the projecting strip are formed in integrity, and directly injection-molded from a high molecular compound.

BRIEF DESCRIPTION OF THE DRAWINGS

The foregoing and other features and advantages of the present invention will be more clearly understood from the following detailed description and the accompanying drawings, in which.

DETAILED DESCRIPTION OF THE PREFERRED EMBODIMENT

Figure 1:
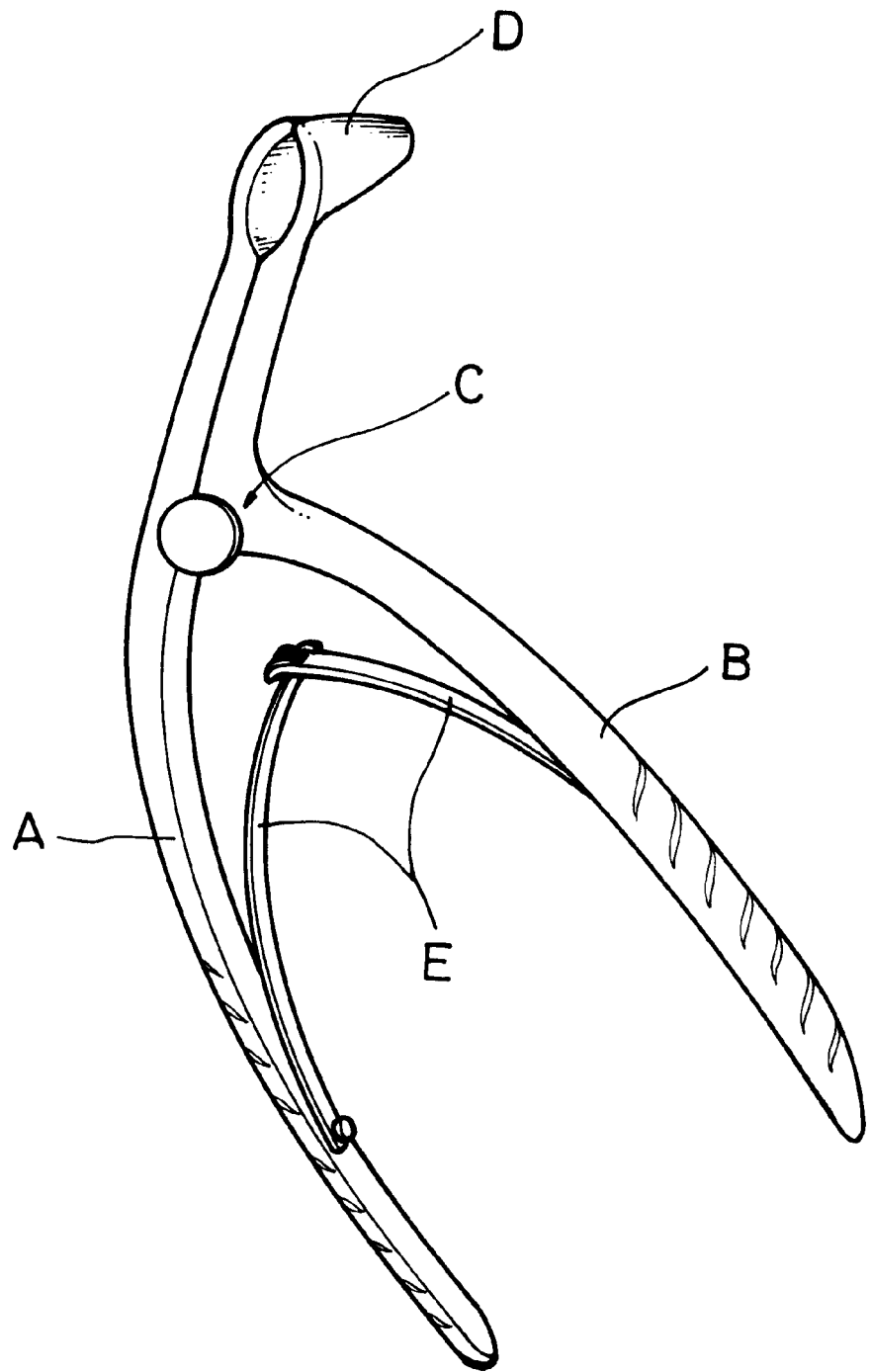
FIG. 1 illustrates a nasal speculum according to the prior art.
Figure 2:
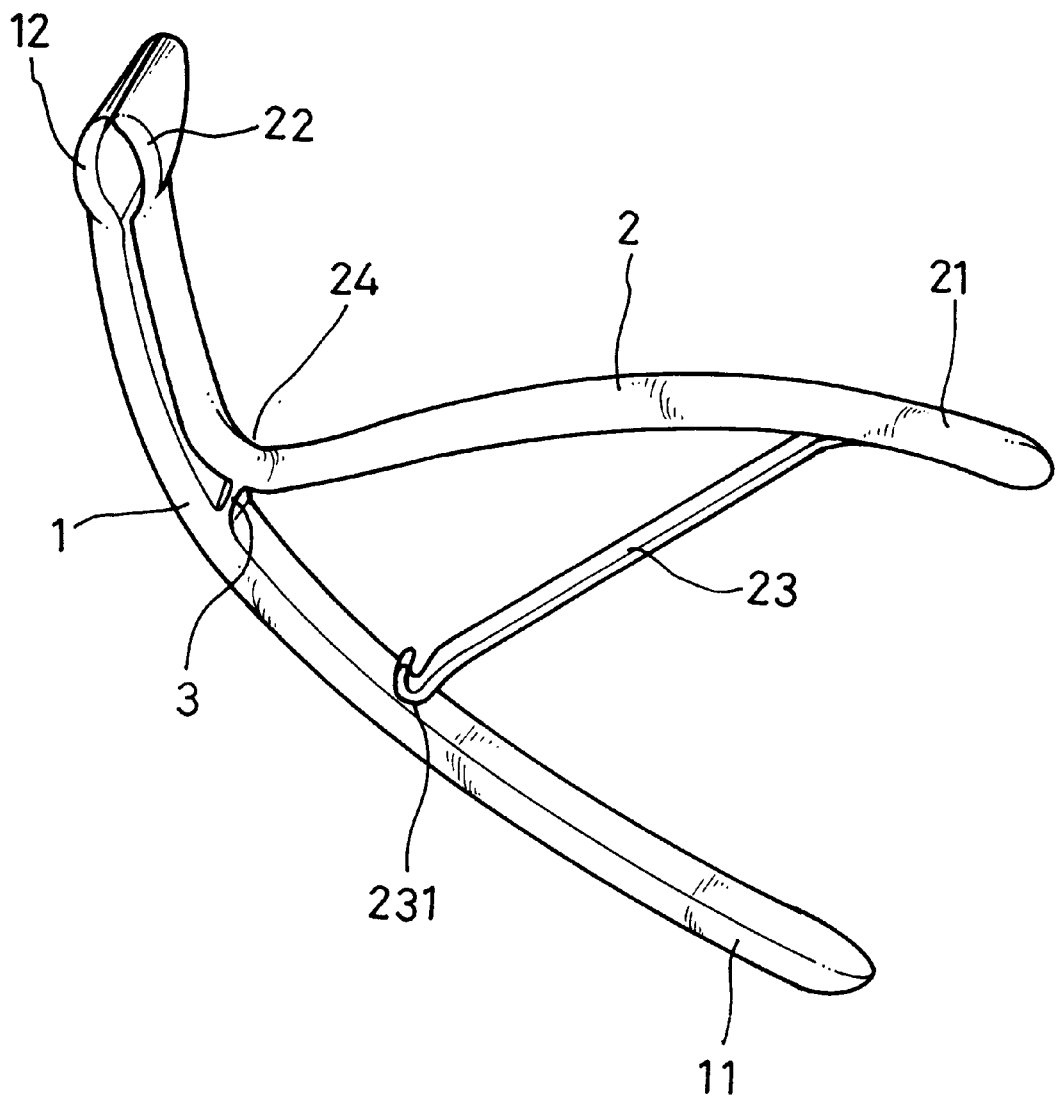
FIG. 2 illustrates a nasal speculum according to the present invention.

Referring to FIG. 2, a nasal speculum according to the present invention is shown comprised of a first rod member 1, a second rod member 2, and a short connecting rod 3 connected between the first rod member 1 and the second rod member 2

The first rod member 1 has a smoothly curved profile comfortable for holding by the hand, a rear end terminating in a hand grip 11, and a front end terminating in an arched tongue 12 of semi-circular cross section. The diameter of the arched tongue 12 is slightly smaller than the nasal passage.

The second rod member 2 has a rear end terminating in a hand grip 21, a front end terminating in an arched tongue 22 of semi-circular cross section, a 90° bend 24 spaced between the hand grip 21 and the arched tongue 22 and connected to the hinge 3, and an oblique projecting strip 23 raised from the inner side thereof toward the first rod member 11 and terminating in an arched tip 231. The arched tip 231 of the projecting strip 23 is stopped at the first rod member 11.

The short connecting rod 3 is flexible, having one end formed integral with the bend 24 of the second rod member 2, and an opposite end formed integral with a middle part of the first rod member 1.

Normally, the projecting strip 23 supports the second rod member 2 on the first rod member 1, enabling the tongues 12 and 22 to be retained closed. When the user squeezes the hand grips 11 and 21 of the rod members 1 and 2 with the hand, the projecting strip 23 is pushed forwards along the inner side of the first rod member 1, the short connecting rod 3 is stretched, and the tongue 22 of the second rod member 2 is turned outwards from the tongue 12 of the first rod member 1 to stretch open the nasal passage. When the user releases the hand grips 11 and 21, the connecting rod 3 immediately returns to its former shape, the projecting strip 23 is turned, backwards along the inner side of the first rod member 1, and the second rod member 2 is forced back to its former position, thereby cause the tongue 22 of the second rod member 2 to be closed on the tongue 12 of the first rod member 1 again.

According to the present invention, the rod members 1 and 2, the short connecting rod 3, and the projecting strip 23 are formed in integrity and directly injection-molded from a high molecular compound, therefore the nasal speculum is suitable for mass production to greatly reduce its manufacturing cost.

While only one embodiment of the present invention has been shown and described, it will be understood that various modifications and changes could be made thereunto without departing from the spirit and scope of the invention disclosed.

What the invention claimed is:

1. A disposable nasal speculum comprising:

a first rod member, said first rod member having a rear end terminating in a hand grip, and a front end terminating in an arched tongue of semicircular cross section;

a second rod member, said second rod member having a rear end terminating in a hand grip, a front end terminating in an arched tongue of semicircular cross section, a bend on the middle between the hand grip and arched tongue of said second rod member, and a projecting strip extended from an inner side thereof toward said first rod member and supporting said second rod member on said first rod member; and a flexible short connecting rod connected between the bend of said second rod member and a part of said first rod member between the hand grip and arched tongue of said first rod member.

2. The disposable nasal speculum of claim 1 wherein said projecting strip of said second rod member has a free end terminating in an arched tip stopped at said first rod member.

3. The disposable nasal speculum of claim 1 wherein the bend of said second rod member is a 90° bend.

4. The disposable nasal speculum of claim 1 wherein said first rod member, said second rod member and said short connecting rod are formed in integrity and injection-molded from a high molecular compound.

* * * * *